United States Patent [19]

Wong et al.

[11] Patent Number: 5,725,851
[45] Date of Patent: *Mar. 10, 1998

[54] METHOD AND COMPOSITIONS FOR TREATING INJURY

[75] Inventors: Grace H.W. Wong, South San Francisco; David V. Goeddel, Hillsborough, both of Calif.

[73] Assignee: Genentech, Inc., South San Francisco, Calif.

[*] Notice: The term of this patent shall not extend beyond the expiration date of Pat. No. 5,370,870.

[21] Appl. No.: 411,224

[22] Filed: Mar. 28, 1995

Related U.S. Application Data

[62] Division of Ser. No. 76,086, Jun. 10, 1993, which is a continuation of Ser. No. 602,849, Oct. 26, 1990, abandoned, which is a continuation-in-part of Ser. No. 507,341, Apr. 10, 1990, abandoned.

[51] Int. Cl.$^6$ .......................... A61K 45/05; A61K 38/21
[52] U.S. Cl. .......................... 424/85.2; 424/85.1; 424/85.4
[58] Field of Search .................................. 424/852, 85.1, 424/85.4

[56] References Cited

U.S. PATENT DOCUMENTS

| | | |
|---|---|---|
| 4,321,832 | 3/1982 | Runyan . |
| 4,861,587 | 8/1989 | Urbaschek et al. . |
| 4,985,241 | 1/1991 | Zimmerman et al. . |
| 5,202,119 | 4/1993 | Clark et al. . |
| 5,370,870 | 12/1994 | Wong ..................... 424/85.1 |

FOREIGN PATENT DOCUMENTS

| | | |
|---|---|---|
| 0 164 965 | 12/1985 | European Pat. Off. . |
| 0 168 214 | 1/1986 | European Pat. Off. . |
| 0 259 863 | 3/1988 | European Pat. Off. . |
| 0 285 448 | 10/1988 | European Pat. Off. . |
| 0 340 005 | 11/1989 | European Pat. Off. . |
| 87/05519 | 9/1987 | WIPO . |
| 90/02183 | 3/1990 | WIPO . |
| 90/10454 | 9/1990 | WIPO . |
| 91/15227 | 10/1991 | WIPO . |

OTHER PUBLICATIONS

Abe et al., *J. Biol. Chem.* 264 (15):8941–8945 (May 25, 1989) "Macrophage Differentiation Inducing Factor from Human Monocyclic Cells is Equivalent to Murine Leukemia Inhibitory Factor".

Carswell et al., *Proc. Natl. Acad. Sci. U.S.A.*, 72(9): 3666–3670 (Sep., 1975) An Endotoxin–Induced Serum Factor that Causes Necrosis of Tumors.

Clark et al., *J. Cell Biochem. Suppl.*, 12A:40 (Jan., 1988) Interplay of Reactive Oxygen Species and Tumor Necrosis Factor in Tissue injury.

Cross et al., *J. Exp. Med.*, 169:2021–2027 (Jun., 1989) Pretreatment with Recombinant Murine Tumor Necrosis Factor α/Cachectin and Murine Interleukin 1 α Protects Mice from Lethal Bacterial Infection.

Fukada et al., *PNAS* 82:8795–8799 (Dec., 1985) Purification and Partial Characterization of a Cholingergic Neuronal Differentiation Factor.

Gearing, et al., *Nucleic Acids Res.*, 16:9857 (1988) Complete Sequence of Murine Myeloid Leukaemia Inhibitory Facotr (LIF).

Gough et al., *Proc. Natl. Acad. Sci. U.S.A.*, 85:2623–2627 (Apr., 1988) Molecular Cloning and Expression of the Human Homologue of the Murine Gene Encoding Myeloid Leukemia–Inhibitory Factor.

Hahn et al., *Proc. Natl. Acad. Sci. U.S.A.*, 82:3814–3818 (Jun., 1985) Use of Monoclonal Antibodies to a Human Cytotoxin for its Isolation and for Examining the Self–Induction of Resistance to this Protein.

Hilton et al., *Anal. Biochem.* 173:359–367 (1988) Purification of a Murine Leukemia Inhibitory Factor from Krebs Ascites Cells.

Holtman et al., *J. Immunol.*, 139:1161–1167 (Aug. 15, 1987) Down Regulation of the Receptors for Tumor Necrosis Factor by Interleukin 1 and 4β–Phorbol–12–Myistate–13–Acetate[1].

Hozumi, *Advances in Cancer Research* 38:121–169 (1983) Fundamentals of Chemotherapy of Myeloid Leukemia by Induction of Leukemia Cell Differentiation.

Hussein et al., *Science*, 249:1564–1566 (Sep., 1990) Protection from Chemotherapy–Induced Alopecia in a Rat Model.

Jacob et al., *Nature*, 331:356–358 (Jan., 1988) Tumor Necrosis Factor–α in Murine Autoimmune 'Lupus' Nephritis.

Lowe et al., *DNA*, 8(5):351–359 (1989) Genomic Cloning and Heterlogous Expression of Human Differentiation––Stimulating Factor.

March et al., *Nature*, 315:641–647 (Jun., 1985) Cloning, Sequence and Expression of Two Distinct Human Interleukin–1 Complementary DNAs (List continued on next page.)

*Primary Examiner*—Lynette F. Smith
*Attorney, Agent, or Firm*—Merchant, Gould, Smith, Edell, Welter & Schmidt

[57] ABSTRACT

D-factor, growth hormone, IL-1, and tumor necrosis factors are employed alone or in combination as synergistic cytoprotective agents for patients exposed to toxic doses of ionizing radiation and/or chemotherapy. Synergistic cytoprotective regimens are provided. Use of D-factor, growth hormone, tumor necrosis factors, and/or IL-1, alone or in synergistic combination, is disclosed for the prevention and treatment of alopecia.

7 Claims, 2 Drawing Sheets

OTHER PUBLICATIONS

Moreau et al., *Nature* 336:690–692 (Dec. 15, 1988) Leukemia Inhibitory Factor is Identical to the Myeloid Growth Factor Human Interleukin for DA Cells.

Mori et al., *Biochem. Biophys. Res. Com.* 160(3):1085–1092 (May, 1989) Purification of a Lipoprotein Lipase–Inhibiting Protein Produced by a Melanoma Cell Line Associated with Cancer Cachexia.

Neta et al., *Fed. Proc.*, 46:1200 (abstract) (Jan., 1987) Comparison of the In Vivo Effects of rIL–1 in Radioprotection, Induction of CSF and of Acute Phase Reactants.

Neta et al., *J. Immunol.*, 136(7):2483–2485 (Apr. 1, 1986) Interleukin 1 is a Radioprotector[1].

Neta et al., *J. Immunol.*, 140:108–111 (Jan. 1, 1988) Interdependence of the Radioprotective Effects of Human Recombinant Interleukin 1α, Tumor Necrosis Factor α, Granulocyte Colony–Stimulating Factor, and Murine Recombinant Granulocyte–Macrophage Colony–Stimulating Factor[1].

Neta et al., *Blood*, 72(3):1093–1094 (Sep., 1988) Cytokins in Therapy of Radiation Injury.

Neta et al., *Lymphokine Research* 5(1):S105–S110 (1986) Cytokines n Radioprotection Comparison of the Radioprotective Effects of IL–1 to IL–2, GM–CSF and IFN$_\gamma$.

Palladino et al., *Intl. J. Radiat. Biol.*, 41:183–191 (1982) γ–Irradiation–Induced Mortality: Protective Effect of Protease Inhibitors in Chickens and Mice.

Schutze et al., *J. Immunol.*, 140:3000–3005 (May 1, 1988) Tumor Necrosis Factor–Induced Changes of Gene Expression in U937 Cells.

Slordahl et al., *Eur. J. Hematology*, 43:428–434 (1989) Radioprotection by Murine and Human Tumor–Necrosis Factor: Dose–Dependent Effects on Hematopoiesis in the Mouse.

Sugarman et al., *Science*, 230:943–945 (Nov. 22, 1985) Recombinant Human Tumor Necrosis Factor–α: Effects on Proliferation of Norman and Transformed Cells in Vitro.

Sullivan et al., *Infect. and Immunity*, 56(7):1722–1729 (Jul., 1988) Inhibition of the Inflammatory Action of Interleukin–1 and Tumor Necrosis Factor (Alpha) on Neutrophil Function by Pentoxifylline.

Tiegs et al., *Biochem. Pharmacol.*, 38(4):627–631 (1989) Tumor Necrosis Factor is a Terminal Mediator in Galactosamine/Endotoxin–Induced Hepatitis in Mice.

Urbaschek et al., *Lymphokine Res.*, 6(3)179–186 (1987) Tumor Necrosis Factor Induced Stimulation of Granulopoiesis and Radioprotection.

Wallach, *J. Immunol.*, 132:2464–2469 (May, 1984) Preparations of Lymphotoxin Induce Resistance to their Own Cytotoxic Effect[1].

Wong et al., *Science* 242:941–944 (Nov., 1988) Induction of Manganous Superoxide Dismutase by Tumor Necrosis Factor: Possible Protective Mechanism.

Wong et al., *Cell*, 58:923–931 (Sep. 8, 1989) Manganous Superoxide Dismutase is Essential for Cellular Resistance to Cytotoxicity of Tumor Necrosis Factor.

Yamamori et al., *Science*, 246:1412–1416 (Dec. 15, 1989) The Cholinergic Neuronal Differentiation Factor from Heart Cells is Identical to Leukemia Inhibitory Factor.

Yuhas et al., *J. Natl. Cancer Inst.*, 42(2):331–335 (Feb., 1969) Differential Chemoprotectin of Normal and Malignant Tissues[1,2,3].

```
HDF   1  P L P I T P V N A T C A I R H P C H N N L M N Q I R S Q L A Q L N G S A N A L F I
MDF   1  P L P I T P V N A T C A I R H P C H G N L M N Q H K N Q L A Q L N G S A N A L F I

HDF  42  L Y Y T A Q G E P F P N N L D K L C G P N V T D F P P F H A N G T E K A K L V E L
MDF  42  S Y Y T A Q G E P F P N N V E K L C A P N M T D F P S F H G N G T E K T K L V E L

HDF  83  Y R I V Y L G T S L G N I T R D Q K I L N P S A L S L H S K L N A T A D I L R G
MDF  83  Y R M V A Y L S A S L T N I T R D Q K V L N P T A V S L Q V K L N A T I D V M R G

HDF 124  L L S N V L C R L C S K Y H V G H V D V T Y G P D T S G K D V F Q K K L G C Q L
MDF 124  L L S N V L C R L C N K Y R V G H V D V P P P D H S D K E A F Q R K L G C Q L

HDF 165  L G K Y K Q I H A V L A Q A F
MDF 165  L G T Y K Q V I S V V Q A F
```

FIG. 2

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 179 amino acids
        ( B ) TYPE: amino acid
        ( D ) TOPOLOGY: linear ( x i ) SEQUENCE DESCRIPTION: SEQ ID NO:1:

```
Pro  Leu  Pro  Ile  Thr  Pro  Val  Asn  Ala  Thr  Cys  Ala  Ile  Arg  His
 1                   5                  10                      15

Pro  Cys  His  Asn  Asn  Leu  Met  Asn  Gln  Ile  Arg  Ser  Gln  Leu  Ala
```

|   |   |   |   | 20 |   |   |   |   | 25 |   |   |   |   | 30 |
|---|---|---|---|----|---|---|---|---|----|---|---|---|---|----|
| Gln | Leu | Asn | Gly | Ser | Ala | Asn | Ala | Leu | Phe | Ile | Leu | Tyr | Tyr | Thr |
|   |   |   |   | 35 |   |   |   |   | 40 |   |   |   |   | 45 |
| Ala | Gln | Gly | Glu | Pro | Phe | Pro | Asn | Asn | Leu | Asp | Lys | Leu | Cys | Gly |
|   |   |   |   | 50 |   |   |   |   | 55 |   |   |   |   | 60 |
| Pro | Asn | Val | Thr | Asp | Phe | Pro | Pro | Phe | His | Ala | Asn | Gly | Thr | Glu |
|   |   |   |   | 65 |   |   |   |   | 70 |   |   |   |   | 75 |
| Lys | Ala | Lys | Leu | Val | Glu | Leu | Tyr | Arg | Ile | Val | Val | Tyr | Leu | Gly |
|   |   |   |   | 80 |   |   |   |   | 85 |   |   |   |   | 90 |
| Thr | Ser | Leu | Gly | Asn | Ile | Thr | Arg | Asp | Gln | Lys | Ile | Leu | Asn | Pro |
|   |   |   |   | 95 |   |   |   |   | 100 |   |   |   |   | 105 |
| Ser | Ala | Leu | Ser | Leu | His | Ser | Lys | Leu | Asn | Ala | Thr | Ala | Asp | Ile |
|   |   |   |   | 110 |   |   |   |   | 115 |   |   |   |   | 120 |
| Leu | Arg | Gly | Leu | Leu | Ser | Asn | Val | Leu | Cys | Arg | Leu | Cys | Ser | Lys |
|   |   |   |   | 125 |   |   |   |   | 130 |   |   |   |   | 135 |
| Tyr | His | Val | Gly | His | Val | Asp | Val | Thr | Tyr | Gly | Pro | Asp | Thr | Ser |
|   |   |   |   | 140 |   |   |   |   | 145 |   |   |   |   | 150 |
| Gly | Lys | Asp | Val | Phe | Gln | Lys | Lys | Lys | Leu | Gly | Cys | Gln | Leu | Leu |
|   |   |   |   | 155 |   |   |   |   | 160 |   |   |   |   | 165 |
| Gly | Lys | Tyr | Lys | Gln | Ile | Ile | Ala | Val | Leu | Ala | Gln | Ala | Phe |   |
|   |   |   |   | 170 |   |   |   |   | 175 |   |   |   |   | 179 |

( 2 ) INFORMATION FOR SEQ ID NO:2:

( i ) SEQUENCE CHARACTERISTICS:
        ( A ) LENGTH: 179 amino acids
        ( B ) TYPE: amino acid
        ( D ) TOPOLOGY: linear ( x i ) SEQUENCE DESCRIPTION: SEQ ID NO:2:

|   |   |   |   |   |   |   |   |   |   |   |   |   |   |   |
|---|---|---|---|---|---|---|---|---|---|---|---|---|---|---|
| Pro | Leu | Pro | Ile | Thr | Pro | Val | Asn | Ala | Thr | Cys | Ala | Ile | Arg | His |
| 1 |   |   |   | 5 |   |   |   |   | 10 |   |   |   |   | 15 |
| Pro | Cys | His | Gly | Asn | Leu | Met | Asn | Gln | Ile | Lys | Asn | Gln | Leu | Ala |
|   |   |   |   | 20 |   |   |   |   | 25 |   |   |   |   | 30 |
| Gln | Leu | Asn | Gly | Ser | Ala | Asn | Ala | Leu | Phe | Ile | Ser | Tyr | Tyr | Thr |
|   |   |   |   | 35 |   |   |   |   | 40 |   |   |   |   | 45 |
| Ala | Gln | Gly | Glu | Pro | Phe | Pro | Asn | Asn | Val | Glu | Lys | Leu | Cys | Ala |
|   |   |   |   | 50 |   |   |   |   | 55 |   |   |   |   | 60 |
| Pro | Asn | Met | Thr | Asp | Phe | Pro | Ser | Phe | His | Gly | Asn | Gly | Thr | Glu |
|   |   |   |   | 65 |   |   |   |   | 70 |   |   |   |   | 75 |
| Lys | Thr | Lys | Leu | Val | Glu | Leu | Tyr | Arg | Met | Val | Ala | Tyr | Leu | Ser |
|   |   |   |   | 80 |   |   |   |   | 85 |   |   |   |   | 90 |
| Ala | Ser | Leu | Thr | Asn | Ile | Thr | Arg | Asp | Gln | Lys | Val | Leu | Asn | Pro |
|   |   |   |   | 95 |   |   |   |   | 100 |   |   |   |   | 105 |
| Thr | Ala | Val | Ser | Leu | Gln | Val | Lys | Leu | Asn | Ala | Thr | Ile | Asp | Val |
|   |   |   |   | 110 |   |   |   |   | 115 |   |   |   |   | 120 |
| Met | Arg | Gly | Leu | Leu | Ser | Asn | Val | Leu | Cys | Arg | Leu | Cys | Asn | Lys |
|   |   |   |   | 125 |   |   |   |   | 130 |   |   |   |   | 135 |
| Tyr | Arg | Val | Gly | His | Val | Asp | Val | Pro | Pro | Val | Pro | Asp | His | Ser |
|   |   |   |   | 140 |   |   |   |   | 145 |   |   |   |   | 150 |
| Asp | Lys | Glu | Ala | Phe | Gln | Arg | Lys | Lys | Leu | Gly | Cys | Gln | Leu | Leu |
|   |   |   |   | 155 |   |   |   |   | 160 |   |   |   |   | 165 |
| Gly | Thr | Tyr | Lys | Gln | Val | Ile | Ser | Val | Val | Val | Gln | Ala | Phe |   |
|   |   |   |   | 170 |   |   |   |   | 175 |   |   |   |   | 179 |

METHOD AND COMPOSITIONS FOR TREATING INJURY

This is a divisional of applications Ser. No. 08/076,086 filed on Jun. 10, 1993, which is a continuation application of Ser. No. 07/602,849 filed on Oct. 26, 1990, (now abandoned) which is a continuation-in-part application of Ser. No. 07/507,341 filed on Apr. 10, 1990, (now abandoned) which applications are incorporated herein by reference.

This invention relates to the treatment of injury, especially injury resulting from radiation or chemotherapy. In particular, it relates to the amelioration of injury to otherwise healthy tissue concomitant with the treatment of cancers and other proliferative disorders, and in the course of bone marrow transplants.

Alopecia is the loss or absence of hair from skin areas where it normally is present; it encompasses male pattern baldness, inflammatory hair loss, drug-induced hair loss, radiation-induced hair loss, and a variety of syndromes. It has recently been reported that IMUVERT, a biologic response modifier derived from the bacterium *Serratia marcescens*, protected against alopecia in 8-day-old rats treated with cytosine arabinoside and doxorubicin, but not against alopecia induced by cyclophosphamide. Hussein et al., Science 249:1564-1566 (28 Sept. 1990).

D-Factor (hereafter "DF") is a known molecule. It is capable of directing the choice of neurotransmitter phenotype made by cultured rat sympathetic neurons, regulates the growth and differentiation of embryonic stem cells and myeloid cells and stimulates bone remodeling and acute-phase protein synthesis in hepatocytes. It has been termed DIA, DIF, DRF, HSFIII, human interleukin DA (HILDA) and LIF (leukemia inhibitory factor). This cytokine has been compared to IL-6 and TGF-beta in that it regulates function, growth and differentiation in the embryo and in the adult in many tissues and cell types, including monocytic cells, megakaryocytes, embryonal stem cells, hepatocytes, adipocytes, osteoblasts and neuronal cells. See Yamamori et al., "Science" 246:1412 (1989), Lowe et al., "DNA" 8(5):351 (1989) and Abe et al., "J. Biol. Chem." 264(15):8941 (1989). DF also is known to induce differentiation of myeloid leukemia cells and therefore has been proposed in the art to be useful in the treatment of myeloid leukemias. DF is currently purified by complex methods not amenable to large scale commercial development (Hilton et al., "Analyt. Biochem." 173:359 [1988]).

Human growth hormone (hGH) is secreted in the human pituitary. Its mature form consists of 191 amino acids and has a molecular weight of about 22,000; its sequence and characteristics are set forth, for example, in *Hormone Drugs*, Geuriguian et al., U.S.P. Convention, Rockville Md. (1982) incorporated herein by reference.

hGH has been used for the treatment of hypopituitary dwarfism, and has been proposed for the treatment of burns, wound healing, dystrophy, bone knitting, diffuse gastric bleeding and pseudarthrosis. The major biological effect of hGH is to promote growth. The organ systems affected include the skeleton, connective tissue, muscles, and viscera such as liver, intestine, and kidneys. Growth hormone exerts its action through interaction with specific receptors on cell membranes. Administration of growth hormone for treatment of pulmonary dysfunction and ventilator dependency has been proposed in U.S. Ser. No. 07/306,978 filed 7 Feb. 1989.

Interleukin-1 (IL-1) is produced by activated macrophages. At least two types exist, designated α and β (March et al., Nature 315:641-647 (1985)). IL-1 mediates a wide range of biological activities; it has been found to stimulate fibroblast proliferation and to induce in these cells the synthesis of collagenase, prostaglandin $E_2$ and interferon beta-2, to decrease in adipocytes the activity of lipoprotein lipase, and to activate osteoclasts.

Tumor necrosis factors (TNFs) are polypeptides produced by mitogen-stimulated macrophages (TNF-α) or lymphocytes (TNF-β) which are cytotoxic to certain malignantly transformed cells but not to certain normal cells (E. A. Carswell et al., Proc. Natl. Acad. Sci. U.S.A. 72:3666, 1975; B. J. Sugarman et al., Science 230:943, 1985; Schultze et al., J. Immunol. 140: 3000, 1988).

TNF-α has been suggested to be responsible for wasting and cachexia in patients with cancer or severe infections, and both TNF-α and TNF-β mediate many other biological effects. TNF is also known to induce MHC antigens. It has been reported that TNF induces MnSOD in various transformed and normal cell lines (Wong et al., Science 242:941, 1988).

It has been suggested repeatedly in the literature that TNF at certain dosages enhances tissue injury caused by reactive oxygen species (see, e.g. Clark et al., J. Cell Biochem. Suppl. 12A, p. 40, January 1988; Sullivan et al., Infect. and Immunity 56(7): 1722-1729, 1988; and Tiegs et al., Biochem. Pharmacol. 38(4): 627-631, 1989).

The literature has reported that TNF-α and other cytokines such as IL-1 may protect against the deleterious effects of ionizing radiation produced during a course of radiotherapy, such as denaturation of enzymes, lipid peroxidation, and DNA damage (Neta et al., J. Immunol. 136(7):2483, 1987; Neta et al., Lymphokine Res. 5:s105, 1986; Neta et al., Fed. Proc. 46:1200 (abstract), 1987; Urbaschek et al., Lymphokine Res. 6:179, 1987; U.S. Pat. No. 4,861,587; Neta et al., J. Immunol. 140:108, 1988), and that TNF treatment accelerates restoration of hematopoiesis in animals compromised by sublethal doses of cytotoxic drugs or irradiation (Neta, et al., Blood 72(3):1093, 1988). It has been reported that pretreatment with TNF protects mice from lethal bacterial infection (Cross et al., J. Exp. Med. 169:2021-2027, 1989). It has also been suggested that administration of subdeleterious amounts of TNF and/or IL-1 may modulate the deleterious effect of subsequent TNF and/or IL-1 administration; this reference further suggests that ionizing radiation may be administered as a sensitizing agent (EPO Appl. EP 0 259 863 A2). It has also been reported that pretreatment of cells with either TNF or IL-1 can confer resistance to killing by subsequent treatment with TNF-α and cycloheximide in combination (Wallach, J. Immunol. 132:2464, 1984; Hahn et al., Proc. Natl. Acad. Sci. U.S.A. 82:3814, 1985; Holtamann et al., J. Immunol 139:1161, 1987; Wong et al., Cell 58:923, 1989). It has been suggested that inadequate endogenous levels of TNF may be involved in the development of diabetes and of lupus erythematosus (Jacob et al., Nature 331:356-358, 1988).

Ionizing radiation damages tissue in large measure by generating oxygen free radicals which in turn readily react with the neighboring tissue components such as nucleic acids and proteins. However, ionizing radiation damages some tissues differently than others. In particular, rapidly proliferating cells such as those of bone marrow are specially sensitive to ionizing radiation, while tissues made up of mature, differentiatal cells are most likely to survive doses of ionizing radiation. This differential effect has been used to treat cancers, which as rapidly proliferating cells are more sensitive to radiation than non-neoplastic cells, and in preparing patients for bone marrow transplantation.

Allogenic bone marrow transplantation typically is used to treat leukemias. In this procedure the patient is treated with chemotherapeutic agents such as cyclophosphamide and with whole body irradiation in order to completely kill the patient's own cancerous bone marrow, after which the bone marrow transplant (from an autologous donor or remission marrow from the patient) is injected into the patient and ultimately lodges in the marrow. Even in successful therapies where the transplant becomes functional, the patient is seriously affected by side effects of the therapy such as infections, radiation damage to non-target tissues, and alopecia. Radiation therapies for other cancers are also fraught with marty of the same adverse reactions, particularly infections and a general weakening and debilitation of patients who are otherwise in no condition to tolerate such injury.

Thus, considerable effort has been expended by the clinical community in attempts to stem radiation injury without also dispensing with the desired therapeutic effects. This effort has been directed at focusing the radiation on the tumors, by attempting to decrease the hypoxic condition in which many solid tumors are found (for example, by hyperbaric oxygen breathing), and by administering cytoprotective substances.

A number of substances have been advocated as cytoprotectors, and some have received clinical use. According to Rubin et al., "Clinical Oncology" p. 70 (1983), sulfhydryl containing compounds such as cysteine and cysteamine have long been known to be radiation protective. It is believed that these sulfhydryl compounds act as freeradical scavengers by entering into the cell and there protecting from radiation damage by reducing the yield of damaging free radicals. Some cytoprotectors are postulated to work by being taken up by normal cells but not in appreciable amounts by target cells such as neoplasms. See Yuhas et al., "J. Natl. Cancer Inst." 42:331 (1969) and Fletcher, "Textbook of Radiotherapy" (1980). Recently, it has been observed that TNF is capable of radioprotection of normal tissues in HIV therapy, but only when administered prior to exposure to radiation (U.S. Ser. No. 07/417,993, filed Oct. 6, 1989 and now pending).

The principal deficiency shared by known cytoprotective agents used clinically to date for this purpose is that they are relatively ineffective in reducing mortality and morbidity after exposure to radiation. This would appear to be consistent with the theory that the adverse clinical effects of radiation are merely the manifestation of cumulative cellular injury caused by highly reactive, transitory free-radical intermediates generated at the time of radiation exposure. Based on this theory, one would expect that post-exposure treatment would be ineffectual since the injury would already have been sustained by the cells. This is particularly the case with cytoprotective agents such as proteins that are not small molecules and therefore must act by initiating intracellular events or by active transport into the cell, or both. The cell's ability to perform these protection-initiating functions would be problematic after a damaging dose of ionizing radiation. Nonetheless, treatment strategies involving a highly effective post-exposure cytoprotective agent would be extremely useful in the therapeutic setting since often times it is difficult to predict the level of radiation dosing that will be safe and effective for any given patient. In addition, such a post-exposure cytoprotective agent would be useful in the event of accidental or unexpected radiation exposure to health workers or others.

Accordingly, it is an object of this invention to provide cytoprotective agents and treatment strategies that are highly effective after exposure to radiation.

It is another object of this invention to provide methods and agents for reducing cellular damage in chemotherapeutic and therapeutic treatments, particularly those employed for HIV infections and neoplasms.

Yet another object of this invention is to provide an agent for prevention or treatment of alopecia.

These and other objects of the invention will be apparent from further consideration of the disclosure.

SUMMARY OF THE INVENTION

Some of the objects of the invention are achieved in a method comprising exposing a subject to a radiation or chemotherapy injury, the improvement comprising administering a cytoprotective dose of an agent or agents selected from the group consisting of DF, and/or GH, alone or in combination with TNF or IL-1, to the subject.

Surprisingly, it was found that DF administered to mice 1 hour after the animals had received a lethal dose of gamma radiation could completely protect the animals from death, and that the effect was related to the dose of DF administered. It has been further found that administration of TNF prior to or concurrent with radiation, followed by administration of DF or GH after exposure to radiation, provided synergistic levels of protection, and that treatment with DF, GH, TNF and/or IL-1, alone or in combination, prevented alopecia associated with radiation and chemotherapy.

This unexpected effect of these agents therefore suggests their use for the treatment of alopecia, in the therapy of tumors in concert with chemotherapy or radiation. In certain situations, it is preferred to include at least one DF or GH administration after the patient is irradiated or exposed to chemotherapy. DF, GH, TNF, and IL-1 may be administered in a course of treatment excluding chemotherapy or radiation, or prior to and/or subsequenct to chemotherapy or irradiation, together with other agents and therapies heretofore employed with chemotherapy or irradiation.

BRIEF DESCRIPTION OF THE FIGURES

FIG. 2 depicts the mature amino acid sequences for human (H) (Sequence ID No. 1) and murine (M) (Sequence ID No. 2) D-factor. Areas of homology are boxed.

DETAILED DESCRIPTION OF THE INVENTION

Figure 1:
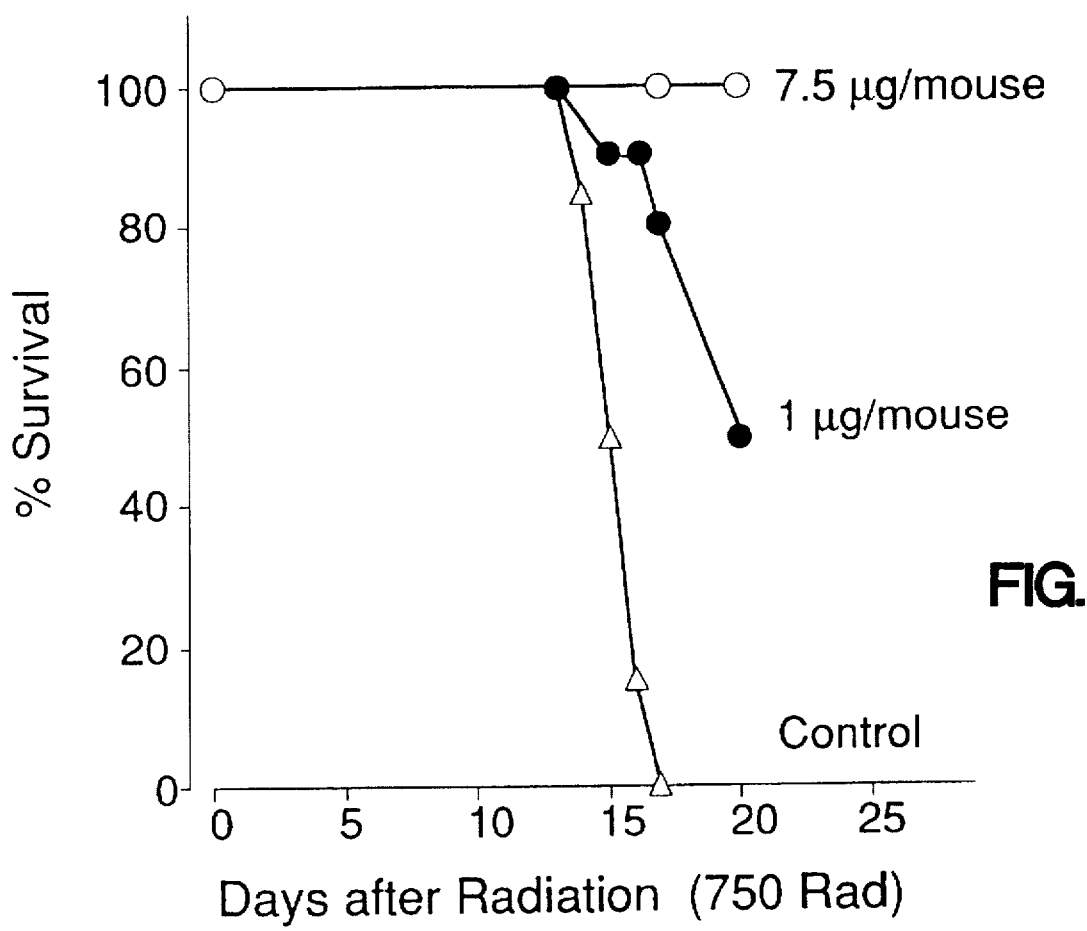
FIG. 1 depicts the 20 day survived of irradiated mice treated with 7.5 micrograms of DF and 1 microgram of DF one hour after irradiation.

Tumor necrosis factor or TNF, as employed herein, refers in general to the various forms of TNF which exhibit one or more biologic properties of tumor necrosis such as tumor cell lysis, inhibition of infectious agents, MHC antigen induction, and neutralization by antibody to TNF-α or TNF-β but not by antibodies to other cytokines. It is believed that gamma interferon is synergistic with TNF in anti-tumor or anti-viral assays for TNF, and may therefore be desirably administered along with TNF in the practice of this invention.

In particular, the tumor necrosis factors useful herein include TNF-α and TNF-β. The former is described in copending EPO Appl. EP 0 168 214 A2 together with methods for its synthesis in recombinant cell culture. Similarly, the latter (previously called lymphotoxin) and suitable recombinant synthesis methods are described in copending EPO Appl. EP 0 164 965 A2. The TNF-α and TNF-β described in these applications include cytotoxic amino acid sequence and glycosylation variants which also are used herein. Of course, TNF-α or TNF-β from non-recombinant sources are also useful in the practice of this invention.

As used herein, the terms "growth hormone" or "GH" denote growth hormone produced from natured source extraction and purification, as well as by recombinant cell culture systems. "hGH" refers to human growth hormone. See, for example, U.S. Pat. No. 4,321,832, specifically incorporated by reference. The terms likewise cover biologically active human growth hormone equivalents, e.g., those differing by one or more amino acids(s) in the overall sequence. Further, the terms as used in this application are intended to cover substitution, deletion and insertion amino acid variants of hGH, or post-translational modifications.

As used herein, "IL-1" denotes interleukin-1 produced from natural source extraction and purification, as well as by recombinant cell culture systems. See, for example, March et al., Nature 315:641–646 (1985)), specifically incorporated by reference. The terms likewise cover biologically active IL-1 equivalents, e.g., those differing by one or more amino acids(s) in the overall sequence. Further, the terms as used in this application are intended to cover substitution, deletion and insertion amino acid variants of IL-1, or post-translational modifications.

The mature amino acid sequences for human (H) and murine (M) DF shown in FIG. 2 are disclosed in EP 285,448, published 5 Oct. 1988 (specifically incorporated by reference herein), especially at FIG. 26, including methods for its production in recombinant cell culture. See also D. P. Gearing et al., Nucleic Acids Res. 16:9857 (1988), and N. M. Gough et al., Proc. Nat. Acad. Sci. U.S.A. 85:2623–2627 (1988). For purposes of this application, DF is defined herein as any polypeptide having (a) cytoprotective activity as defined below and (b) amino acid sequence which is homologous to either amino acid sequence of FIG. 2.

Homologous, as to DF for example, for the purposes herein means that the candidate polypeptide comprises the epitope of DF that is functional in conferring cytoprotection on experimented animals, or functionally conserved amino acid variants thereof. Identification of this epitope is a matter of routine experimentation. Most typically, one would conduct systematic substitutional mutagenesis of the DF molecule while observing for reductions or elimination of cytoprotective activity. This is commonly accomplished by sequentially substituting each residue of the native DF sequence with alanine. Preferably, the residues to be substituted will be those which are (1) identically conserved among animal species, (2) located on disulfide bonded loops, and (3) hydrophilic in nature. Domains containing more than 4 identically conserved residues among animal species and which are not found within about 3 residues of a site of glycosylation are to be preferred for mutagenesis. Preferred regions for mutagenesis are 12–25, 34–60 and 121–143 of the FIG. 2 sequences. In any case, it will be appreciated that due to the size of DF most substitutions will have no effect on DF activity, but if some effect is seen it will be modestly agonistic or antagonistic. The great majority of DF variants will possess at least some cytoprotective activity, particularly if the substitution is conservative. Conservative substitutions are substitutions from the same classes, defined as acidic (Asp, Glu), hydroxy-like (Cys, Ser, Thr), amides (Asn, Gln), basic (His, Lys, Arg), aliphatic-like (Met, Ile, Leu, Val, Gly, Ala, Pro), and aromatic (Phe, Tyr, Trp). The 9 C-terminal hydrophobic residues should only be substituted, if at all, with other hydrophobic residues. The first 3 N-terminal residues may be deleted or freely substituted, and may include a serine residue inserted at the N-terminus.

Alternatively, or in addition, the active site is identified by raising antibodies against the intact native DF, screening for neutralizing antibodies, and determining the site to which the neutralizing antibodies bind. Neutralizing antibodies against DF also would find use in diagnostic immunoassays for DF, especially when used in a sandwich-type immunoassay in concert with a non-neutralizing antibody directed against another DF epitope.

Homologous sequences generally will be greater than about 30 percent homologous on an identical amino acid basis, ignoring for the purposes of determining homology any insertions or deletions from the candidate molecule in relation to either native sequence of FIG. 2. Homologies of about 50, 70 and 90% are also included within the scope hereof so long as the molecules possess the requisite cytoprotective activity.

The cytoprotective agents discussed herein, e.g. DF, hGH, TNF, IL-1, also includes glycosylation variants as well as unglycosylated forms of the agents, fusions of the agents with heterologous polypeptides, and fragments of the agents, again so long as the variants possess the requisite cytoprotective activity.

Cytoprotective activity is defined as the statistically significant ($P$ greater than 0.05) ability of an intraperitoneal dose of the candidate cytoprotective agent DF and/or hGH, delivered concurrent with or up to about twenty-four hours after irradiation or chemotherapy, to reduce mortality or morbidity of the subject animals. However, it will be understood that in therapeutic use it is unlikely, barring accidental overdose, that DF would be employed to ameliorate a lethal dose of radiation. Instead, for example, the typical doses for different human tumors range from 2,000 rad in 2 weeks to 8,000 rad in 8 weeks, with the vast majority of tumors receiving doses between 4,500 and 7,500 rad. These doses are typical therapeutic doses. While they far exceed any ambient radiation they generally are not lethal when administered properly over time, but they are characterized by minor to severe side effects which can lead to death. DF and/or hGH, alone or in conjunction with pretreatment with TNF and/or IL-1, is used either to increase the net irradiation or chemotherapy dose, with clinical tolerance of essentially the same toxicity but an advantage in therapy, or to use conventional doses but with amelioration of morbidity and mortality.

Chemotherapy is defined to be the administration of an agent known to exert a toxic effect on rapidly proliferating cells in comparison to differentiated, mature and slower growing cells. Such agents are well known in the therapy of cancers and other proliferative disorders. They include, for example, adriamycin, chlorambucil, daunomycin, cyclophosphamide, methotrexate, cisplatin, procarbazine, protein synthesis inhibiting agents such as actinomycin-D, bleomycin, 5-azacytidine, vincristine, alkylating agents, dicarbazine, fluorouracil, hydroxyurea, mitomycin-C, nitrosoureas, busulfan, mithramycin, vinblastine, vindesine, and antimetabolites such as mitrosoureas, cytarabine, and mercaptopurine. These cytotoxic agents cause nausea and vomiting, fever, alopecia, chills and malaise and fatigue. Treatment with a cytoprotective regimen as provided herein (DF and/or hGH, alone or in conjunction with treatment with TNF and/or IL-1) reduces the toxicity of such cytotoxic agents and therefore is useful as companion treatment, before and/or after a regimen of chemotherapy.

The amount of DF, GH, TNF and/or IL-1 which is used will depend upon the irradiation or chemotherapy protocol, the condition of the patient, the activity of the agent used, the administration route, and other influences that will be appreciated by the ordinary artisan. In mice, a dosage of about 7.5 micrograms of DF ip/mouse is acceptable, with about 0.5 micrograms to 20 micrograms per day being the range from the lowest level that is marginally effective for cytoprotection to a safe and adequate upper limit. Obviously, the dose will differ for other animals and humans and will vary depending upon administration routes. Pretreatment effective amounts of IL-1 administered to mice range between about 0.5 to 25 nanograms per gram of body weight of mouse.

For hGH, a suitable dosage for human administration ranges from 0.001 mg per kg of bodyweight per day to about 0.2 mg per kg of bodyweight per day. Generally, daily dosages of hGH will be from about 0.05 mg per kg of bodyweight per day. Normally, from 0.07 to 0.15 mg/kg, in one or more applications per day, is effective to obtain the desired result. In an alternative approach, the hGH, particularly where formulated in a timed-release form, may be administered less frequently, i.e., every other day or every third day for certain indication, such as alopecia. It is presently preferred the hGH be administered within 0 to 24 hours following exposure to chemotherapy or irradiation.

The therapeutically effective dosage of TNF to be administered to a human patient or human tissue generally will range from about 1–250 µg/m$^2$ per dose, and preferably from about 1–10 µg/m$^2$, and most preferably 10 µg/m$^2$, although the dose of the TNF (as with the other cytoprotective agents) administered will be dependent upon the species of the patient, the properties of the TNF employed, e.g. its activity and biological half-life, the concentration of the TNF in the formulation, the rate of dosage, the clinical tolerance of the patients involved, the pathological condition of the patients and the like, as is well within the skill of the physician. It will be appreciated that the practitioner will adjust the therapeutic dose in line with clinical experience for any given TNF. Preferably, the TNF is administered intravenously or intramuscularly.

Similar dosage ranges and regimens apply for the treatment of alopecia not associated with radiotherapy or chemotherapy.

The DF, hGH, TNF and IL-1 should be of pharmaceutical grade, i.e., greater than about 95% pure by weight of protein. It is formulated into conventional carriers such as isotonic saline at a concentration suitable for delivery of a cytoprotective dose in a reasonable volume of carrier, typically ranging from several mls. for bolus injection to severed hundred mls. for administration by iv infusion.

In accordance with this invention, DF, hGH, TNF and/or IL-1 is used together with radiation and/or chemotherapy in the treatment of leukemias as well as other cancers known to be susceptible to radiation treatment (e.g., lymphoma, seminoma, dysgerminoma, squamous cell cancer of the oropharyngeal, glottis, bladder, skin and cervical epithelia, adenocarcinomas of the alimentary tract, and astrocytomas) and chemotherapy (e.g. ALL, Wilm's tumor, Ewings sarcoma, retinoblastoma, rhabdomyosarcoma, Hodgkin's disease, DHL, Burkitt's lymphoma, testicular carcinoma, choriocarcinoma, neuroblastoma, acute leukemia, myeloma, lymphomas, small cell lung cancer, breast, stomach, or adrenal cancer, malignant insulinoma, osteogenic sarcoma, CLL, CGL, prostate, endometrial or cervical carcinoma, endocrine gland carcinomas, malignant carcinoids, sarcomas, brain cancers, non-oat cell carcinoma, and carcinoma of the head and neck, thyroid, colon, rectum, liver and bladder.

While it was known to use individually some of the cytoprotective agents described herein with radiation or chemotherapy, or has been proposed to be useful in the treatment of myeloid leukemias, the combination of agents claimed herein unexpectedly and surprisingly offers the significant advantage of synergistic and greatly enhanced protection against radiation and chemotherapy toxicity as well. In addition, the cytoprotective agents and regimens claimed herein find use in accordance with this invention, and the same advantages are obtained, in the radiotherapy or chemotherapy of non-myeloid leukemic cancers, in non-therapeutic (e.g. accidental) irradiation, in bone marrow transplantation and in any other process in which radiation exposure occurs at doses greater than ordinary ambient levels, or in which chemotherapy is used. As noted above, a significant advantage of this invention is that DF and/or hGH can be administered following irradiation or chemotherapy and still achieve cytoprotection.

DF and hGH is administered prior and/or after exposure to cytotoxin. DF and hGH can be administered after chemotherapy or irradiation and still obtain therapeutic benefit. DF and hGH have been demonstrated effective up to 24 hours after exposure to radiation or chemotherapy. It is likely that each agent will be effective when administered at greater and lesser lengths of time after exposure to cytotoxin, although efficacy will vary depending upon the dose and time course of chemotherapy or irradiation, the amount, delivery route and activity of the DF and/or hGH and the condition and species of the subject. The time and frequency of administration of the agent, like the dose and administration route, will be optimized based on clinical experience.

DF is used together with other agents conventionally employed in chemotherapy and radiotherapy, e.g. thiol therapeutics.

DF is obtained by recovery from native sources (cultures of non-recombinant cell lines) or is produced in recombinant cell culture as described in EP 285,448 or Lowe et al. (supra).

EXAMPLE 1

Tissue culture fluid containing DF prepared according to Lowe et al. was concentrated approximately 80 fold using a Pellicon concentrator. The concentrated tissue culture fluid containing DF was dialyzed overnight into 25 mM Tris-HCl, pH 8.0 at 4° C. DF was then purified using a DEAE Sepharose Fast Flow column equilibrated in 25 mM Tris-HCl, pH 8.0. DF was then further purified by S-Sepharose Fast Flow. DF was eluted from the S-Sepharose Fast Flow column using a 0–0.4M NaCl gradient in 25 mM succinate, pH 4.0. Fractions containing DF were pooled, concentrated and diafiltered into 25 mM succinate, pH 4.0, 0.1M NaCl. The concentrated DF pool was then loaded onto a Sephacryl S-300 column equilibrated in 25 mM succinate, pH 4.0, 0.1M NaCl. The Sephacryl S-300 fractions containing DF were pooled and dialyzed into 25 mM bis-Tris propane, pH 6.5. Endotoxin (LAL) was removed by Q-Sepharose Fast Flow. DF was dialyzed into 25 mM succinate, pH 4.0 and stored at 4° C. at a concentration of 0.39 mg/ml.

EXAMPLE 2

This example describes an improved method for DF purification. DF-containing tissue culture fluid was concentrated using either a 2 liter stirred cell concentrator or a Pellicon concentrator. The concentrated tissue culture fluid was dialyzed overnight into 25 mM succinate, pH 4.0.

Precipitation from the DF solution occurred in the absence of acetonitrile or phenyl-silica. The supernatant was carefully removed from the precipitated proteins by either centrifugation and/or decanting of the supernatant. The dialyzed supernatant was further purified by chromatography on S-Sepharose Fast Flow. DF was eluted using a 0–0.4M NaCl gradient in 25 mM succinate, pH 4.0. DF containing fractions (typically at about 0.1–0.3M NaCl) were pooled and concentrated approximately 8-fold in an Amicon stirred cell. The concentrated DF pool was further purified on a Sephacryl S-300 column equilibrated with 25 mM succinate, pH 4.0, 0.1M NaCl. Fractions (at about 40–45 kD) containing D-factor were pooled and stored at 4° C.

EXAMPLE 3

This study was conducted at the U.S. Armed Forces Radiobiology Institute by Dr. Ruth Neta. DF prepared by the method of Example 1 was formulated in phosphate buffered saline at 1 microgram/ml. C3H/HEJ mice were irradiated with 750 rads from a gamma radiation source. Groups of mice were injected intraperitoneally one hour after irradiation with DF doses of either 7.5 micrograms or 1 microgram and the animals observed for mortality over a period of 20 days. As can be seen from FIG. 1, all of the control animals had died by 17 days post-irradiation, whereas only about half of the 1 microgram cohort had expired at 20 days and none of the animals receiving 7.5 micrograms had died.

EXAMPLE 4

This study was conducted at the Memorial Sloan Kettering Cancer Center by Dr. Malcolm A. S. Moore. Hematopoietic protection in vivo in mice against high dose cyclophosphamide (Cytoxan brand) provided by a pre- or post injection of DF was compared. Myelosuppression was monitored by daily white blood cell counts and absolute neutrophil counts (ANC). The dose of Cytoxan used (350 mg/kg) is lethal in 50% of mice after one dose and 90% fatal after two in the absence of supportive therapy. Daily IL-1 treatment had been shown to significantly reduce the duration of the neutrophil nadir, accelerate neutrophil regeneration and enhance survived.

24 male Balb/c mice (Jax—average weight 23 grams) were divided into 8 groups and treated as follows:

A. Control i.p. injection of 350 mg/kg Cytoxan in 0.2 ml on Day 2.

B. 5 µg DF given i.p. on Day 1, followed 24 hours later by 350 mg/kg Cytoxan i.p.

C. i.p. injection of 350 mg/kg Cytoxan on Day 2 followed 6 hours later by 5 µg DF i.p. daily for 4 days.

Figure 3:
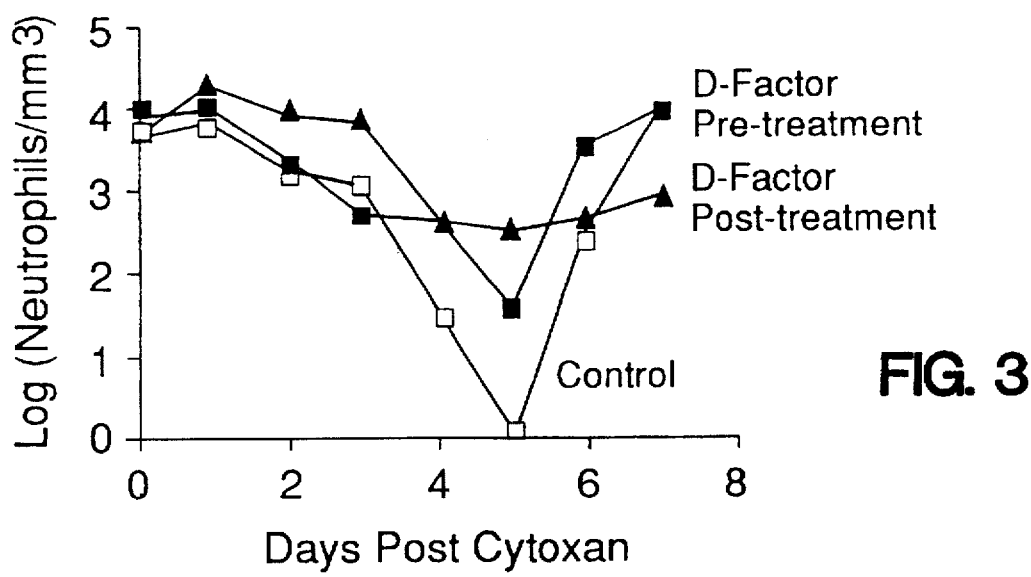
FIG. 3 depicts DF's proctective effects on neutrophil recovery in chemotherapeutically treated mice.

Data from this experiment is shown in FIG. 3. DF given pre-Cytoxan had no significant effect (except perhaps at day 6 after Cytoxan) on either neutrophils or lymphocytes. DF given post-Cytoxan significantly reduced (or eliminated) the rapid drop in neutrophils and lymphocytes in the first 5 days post-Cytoxan and was significantly better in this regard than IL-1, G-CSF (data not shown). DF reduced the absolute nadir of ANC but did not accelerate regeneration.

EXAMPLE 5

This experiment was done by Dr. Adel A. Yunis at the University of Miami School of Medicine. Protection in young male rats against cytosine arabinoside (ARA-C)-induced alopecia was compared for IMUVERT (a biologic response modifier derived from the bacterium *Serratia marcescens*), recombinant murine TNF-α, human IL-1 beta, human DF and hGH, following the procedures described in Hussein et al., Science 249:1564–1566 (28 Sep. 1990), hereby incorporated by reference. Thirty-six 8-day-old rats were randomly divided into 6 groups and treated for a total of seven consecutive days. Each group received 20 mg/kg per day ARA-C at noon on each day. Additionally and three hours prior to the ARA-C administration, Group I received 0.1 ml buffer, group II received 25 µg/day IMUVERT, Group III received 2.5 µg/day murine TNF-α, Group IV received 0.5 µg/day human IL-1 beta, Group V received 10 µg/day DF, and Group VI received 10 µg/day hGH. Alopecia data were recorded on day 7 of the experiment, although unpublished data confirm the same results on day 10.

Results. Alopecia to a degree of total hair loss was reported for all 6 of the control animals. The 6 rats treated with IMUVERT, one rat treated with TNF, one rat treated with DF, and the 6 treated with IL-1 beta had no detectable alopecia. Four rats treated with DF had mild alopecia defined as less than 50% hair loss and 1 DF-treated rat had moderate alopecia, defined as moderate alopecia with more than 50% hair loss. One rat treated with hGH had mild alopecia, one rat treated with hGH had moderate alopecia, and 4 rats treated with hGH had severe alopecia or total hair loss. From this data it may be seen that TNF, IL-1, DF or hGH treatment provides protection against chemotherapeutic alopecia.

---

We claim:

1. A method for treating injury resulting from radiation or chemotherapy comprising:

administering to a subject a synergistic cytoprotective dose of at least two members selected from the group consisting of D-factor, growth hormone (GH), tumor necrosis factor (TNF) and IL-1 to the subject, provided that where TNF and IL-1 are both administered a third member is also administered, wherein the cytoprotective dose is administered prior to, during, or after the subject is exposed to radiation or chemotherapy.

2. The method of claim 1 wherein the subject has myeloid leukemia.

3. The method of claim 1 wherein the subject has a non-leukemic tumor.

4. The method of claim 1 wherein the subject undergoes a bone marrow transplant following irradiation or chemotherapy.

5. The method of claim 1 wherein D-factor or GH is administered after exposure to a radiation or chemotherapy injury.

6. The method of claim 1 wherein TNF or IL-1 is administered prior to or concurrent with exposure to a radiation or chemotherapy injury.

7. The method of claim 1 wherein the TNF is TNF-$\alpha$.

* * * * *

UNITED STATES PATENT AND TRADEMARK OFFICE
CERTIFICATE OF CORRECTION

PATENT NO.    : 5,725,851
DATED         : March 10, 1998
INVENTOR(S)   : Wong et al.

It is certified that error appears in the above-identified patent and that said Letters Patent is hereby corrected as shown below:

Column 1,
Line 4, insert -- application -- after the word "This".
Line 4, "applications" should read -- co-pending application --.

Column 2,
Line 61, "differentiatal" should read -- differentiated --.

Column 3,
Line 11, "marty" should read -- many --.

Column 4,
Line 38, "survived" should read -- survival --.

Column 5,
Line 38, "experimented" should read -- experimental --.

Column 7,
Line 48, "severed" should read -- several --.

Column 8,
Line 19, "is" should read -- can be --.

Column 9,
Line 42, "survived" should read -- survival --.

Sequence Listing Number 1,
Line 8, "(xi)" should read -- (iv) --.
Line 8, insert -- human DF -- after the numeral "NO:1:".

UNITED STATES PATENT AND TRADEMARK OFFICE
CERTIFICATE OF CORRECTION

PATENT NO. : 5,725,851
DATED : March 10, 1998
INVENTOR(S) : Wong et al.

It is certified that error appears in the above-identified patent and that said Letters Patent is hereby corrected as shown below:

<u>Sequence Listing Number 2,</u>
Line 6, "(xi)" should read -- (iv) --.
Line 6, insert -- murine DF -- after the numeral "NO:2:".

Signed and Sealed this

Thirteenth Day of August, 2002

Attest:

Attesting Officer

JAMES E. ROGAN
*Director of the United States Patent and Trademark Office*